United States Patent [19]

Ng et al.

[11] Patent Number: 5,108,920

[45] Date of Patent: Apr. 28, 1992

[54] RETROVIRUS ISOLATED FROM HUMAN LYMPHOMA CELL LINES

[75] Inventors: Valerie L. Ng, Piedmont; Michael S. McGrath, Burlingame; Gregory R. Reyes, Palo Alto, all of Calif.

[73] Assignees: Regents of the University of California, Oakland; Genelabs Incorporated, Redwood City, both of Calif.

[21] Appl. No.: 361,855

[22] Filed: Jun. 5, 1989

[51] Int. Cl.[5] .......................... C12N 7/02; C12N 7/00; C12N 5/08; C12N 5/00
[52] U.S. Cl. ................................ 435/239; 435/240.2; 435/235.1
[58] Field of Search ...................... 435/235, 240.2, 239, 435/235.1, 240.1

[56] References Cited

PUBLICATIONS

Rashud et al., Anti Cancer Res. 5(6):633, 1985.
Rashud et al., Anti Cancer Res. 6(3 Part A):383, 1986.
Goodacre et al., Exp. Hermatology 16(6):562, 1988.
Ford et al., Lab. Invest. 60(1):29A, 1989.
Goodacre et al., J. Cell. Biochem. 13B:315, 1989.

*Primary Examiner*—Richard A. Schwartz
*Assistant Examiner*—Johnny F. Railey, II
*Attorney, Agent, or Firm*—Peter J. Dehlinger; Gary R. Fabian

[57] ABSTRACT

A novel retrovirus isolated from human lymphoma cells is disclosed. The retrovirus is characterized by a C-type retroviral particle of approximately 100 nm diameter; and an approximately 27,000 molecular weight p24 core protein. Also disclosed are cell lines from which the virus can be obtained and screening methods for detecting the presence of the virus in human sera.

8 Claims, 8 Drawing Sheets

Fig. 7A  2F7
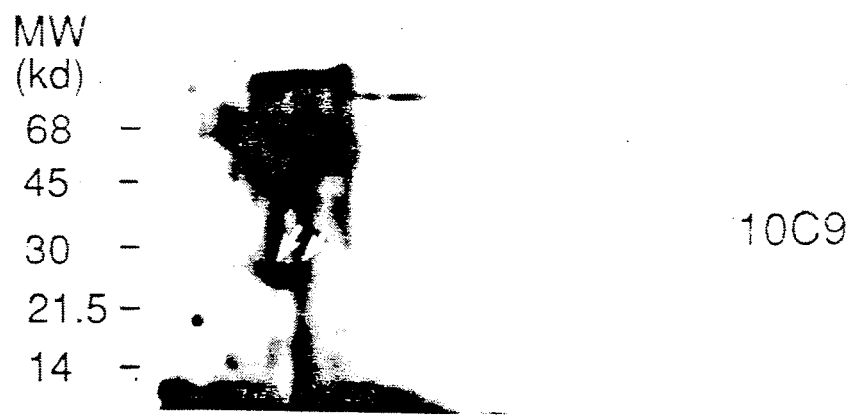
Fig. 7B  10C9
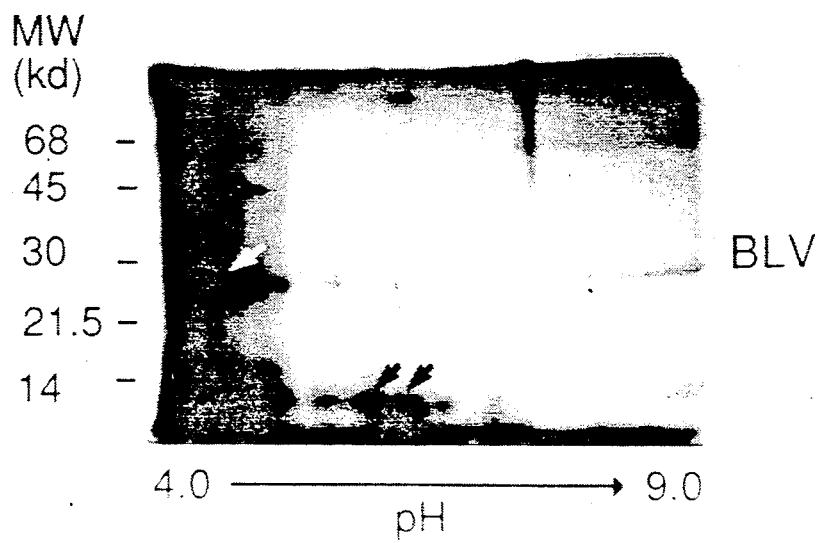
Fig. 7C  BLV A: PID      D: A-NHL
B: NHS      E: PREGNANT WOMAN
C: ATLL     F: IVDUs

RETROVIRUS ISOLATED FROM HUMAN LYMPHOMA CELL LINES

This invention was made with Government support under Grant No. PO1-AI24286 awarded by the National Institute of Health. The Government has certain rights in this invention.

FIELD OF THE INVENTION

The present invention relates to human retroviruses, and in particular, to a new type of retrovirus associated with human, non-Hodgkins lymphoma.

REFERENCES

Burny A, Cleuter Y, Kettman R et al. Cancer Surv 6:139-159 (1987).

Burny A., Bruck C., Cleuter Y. et al. in Animal Models of Retrovirus Infection and Their Relationship to AIDS, Salzman L. A. ed, Academic Press, Inc., Orlando, Fla. (1986).

Cleveland D. W., Fischer S. G., Kirschner M. W., Laemmli U. K. J Biol Chem 252:1102-1106 (1977).

Donham K. J., VenDerMaaten M. J. et al., J Natl Cancer Inst 59:851-853 (1977).

E. G. Feigal, P. Lekas, J. H. Beckstead, G. Reyes, L. Kaplan, M. S. McGrath, in Human Retroviruses, Cancer and AIDS, D. Bolognesi, ed., (New York: Alan R. Liss), pp. 213-228 (1988).

Ferrer J. F., Kenyon S. J., Gupta P. Science 213:1014-1016 (1981) 1981.

Fraker P. J., Speck J. C. Biochem Biophys Res Comm 80:849-857 (1978).

R. C. Gallo, V. S. Kalyanaraman, M. G. Sarngadharan, A. Sliski, E. C. Vonderheid, M. Maeda, Y. Nakao, K. Yamada, Y. Ito, N. Gutensohn, S. Murphy, P. A. Bunn, Jr., D. Catovsky, M. F. Greaves, D. W. Blayney, W. Blattner, W. F. Jarrett, H. zur Hausen, M. Seligmann, J. C. Brouet, B. F. Haynes, B. V. Jegasothy, E. Jaffe, J. Cossman, S. Broder, R. I. Fisher, D. W. Golde, M. Robert-Guroff, Cancer Res 43,3892 (1983).

A. D. Hoffman, B. Banapour, J. A. Levy, Virology 147:326 (1985).

Houmard J., Drapeau G. R. Proc Natl Acad Sci USA 69:3506-3509 (1972).

C. D. Kaplan, D. Abrams, E. Feigal, M. S. McGrath, J. Kahn, P. Neville, J. Ziegler, P. Volberding, JAMA, in press.

Kopchick J. J., Karshin W. L., Arlinghaus R. Virol 30:610-623 (1979).

Korsmeyer, S. J. et al, Proc Nat Acad Sci, USA, 78:7096 (1981).

Laemmli U. K. Nature 227:680-685 (1970).

A. M. Levine, P. R. Meyer, M. K. Begandy, J. W. Parker, C. R. Taylor, L. Irwin, R. J. Lukes, Ann Intern Med 100,7 (1984).

A. M. Levine, P. Gill, P. Meyer, R. L. Burkes, R. Ross, R. D., Dworsky, M. Krailo, J. W. Parker, R. J. Lukes, S. Rasheed, JAMA 254,1921(1985).

McGrath M. S., Witte O., Pincus T., Weissman I. L. J Virol 25:823 (1978).

Mann D. L., DeSantis P., Mark G., et al., Science 236:1103-1106 (1987).

Markwell M. A. K., Fox C. F. Biochem 17:4807-4817 (1978).

Miyoshi I., Kubonishi I., Yoshimoto S., Shiraishi Y. Gann 72:978 (1981).

Ng V. L., Kopchick J. J., Karshin W. L., Wood T. G., Arlinghaus R. B., J Gen Virol 47:161-170 (1980).

O'Farrell P. Z., Goodman H. M., O'Farrell P. H. Cell 1133-1142 (1977).

Palker T. J., Clark M. E., Sarngadharan M. G., Matthews T. J. J Virol Meth 18:243-256 (1987).

Poplack, T. A. Waldmann, P. Leder, PNAS 78,7096(1981).

M. Popovic, et al. Science 219,856-859(1983). V. Manzari, et al. Science 238,1581-1583 (1987).

Sagata N, Yasunaga T, Tsuzuku Kawamura J et al. Proc Natl Acad Sci US 82:677-681 (1985).

H. Suto, T. Okachi, Int. J. Cancer 37, 395-400 (1986).

E. M. Southern, Anal Biochem 62, 317(1974).

Thomas, et al, PNAS 77, 5201 (1980).

Tomita S., Ambrus Jr. J. L., Volkman D. J. et al., J Exp Med 393-398 (1985).

Wong-Staal F., Gallo R. C. Blood 65:253-263, 1985; Essex M., McLane M. F., Kanki P. et al., Cancer Res (suppl.) 4534s-4538s (1985).

Yoshida, I., Miyoshi, Y. Hinuma, Proc Natl Acad Sci USA 79,2031 (1982).

Yoshida M., Biochim Biophys Acta 907:145-161 (1987).

J. L. Ziegler, W. L. Drew, R. C. Miner, L. Mintz, E. Rosenbaum, J. Gershow, E. T. Lennette, J. Greenspan, E. Shillitoe, J. Beckstead, C. Casavant, K. Yamamoto, Lancet 2,631 (1982).

BACKGROUND OF THE INVENTION

Over the past several years, a marked increase in the incidence of high grade B cell lymphoma in individuals at risk for AIDS has been noted (Ziegler, Kaplan).

There is some evidence that HTLV-I infection may play a role in B-cell lymphogenesis. It has been reported that the sera of a subgroup of patients with AIDS-associated lymphoma contained both anti-HIV antibodies and antibodies reactive with the envelope glycoproteins (gp45/61) of HTLV-I (Feigal). Mann and colleagues have shown that B-cells isolated from the primary lymphoma tissue obtained from two patients with HTLV-I infection made immunoglobulins which reacted specifically with HTLV-I viral antigens (Mann). Also, immortalized B-cell clones have spontaneously arisen from in vitro cultivation of peripheral blood mononuclear cells from patients with HTLV-associated adult T-cell lymphoma/leukemia (ATLL).

In view of the increasing incidence of AIDS-related human lymphoma, it would be valuable to identify the viral etiological agent. This would allow screening of blood supplies for the presence of the viral agent, lead to possible preclinical treatment of the disease, and allow development of vaccines or antibodies against the agent.

SUMMARY OF THE INVENTION

The present invention includes, in one aspect, a human retrovirus associated with human B-cell, non-Hodgkins lymphoma, which is isolated from cultured B-lymphoma cells obtained from HIV-I infected patients. The retrovirus is characterized by (a) a round, nucleoid, C-type retroviral particle of approximately 100 nm diameter, and (b) an approximately 27,000 molecular weight p24 core protein.

In another aspect, the invention includes a human retrovirus associated with human B-cell, non-Hodgkins lymphoma, and which is characterized by (a) a round, nucleoid, C-type retroviral particle of approximately 100 nm diameter, (b) an approximately 27,000 molecular weight p24 core protein, and (c) proteins of approximately 31,000 and 55,000 molecular weight.

In another aspect, the invention includes a human retrovirus associated with human B-cell, non-Hodgkins lymphoma, and which is characterized by a (a) a round, nucleoid, C-type retroviral particle of approximately 100 nm diameter, (b) an approximately 27,000 molecular weight p24 core protein, and (c) a p24 core protein tryptic digest map which contains the nine tryptic fragments which are common to the tryptic digest fragments shown in FIGS. 9B and 9C below.

In one exemplary retrovirus of this type, the p24 core protein tryptic digest map contains the eleven tryptic digest fragments shown in FIG. 9C. This virus may be obtained from a lymphoma cell line designated 10C9. In another exemplary retrovirus of this type, the p24 core protein tryptic digest map contains the ten tryptic digest fragments shown in FIG. 9B. This virus may be obtained from a lymphoma cell line designated 2F7.

The invention further includes a lymphoma cell line obtained from a suspension of lymph node lymphocytes from a patient with AIDS associated, non-Hodgkins lymphoma. The cell line contains a retrovirus characterized by (a) a round, nucleoid, C-type retroviral particle of approximately 100 nm diameter, (b) an approximately 27,000 molecular weight p24 core protein, (c) proteins of approximately 31,000 and 55,000 molecular weight; and (d) a p24 core protein tryptic digest map which contains the nine tryptic fragments which are common to the tryptic digest fragments shown in FIGS. 9B and 9C.

Also included in the invention is a method of screening human sera for the presence of a human retrovirus associated with human B-cell, non-Hodgkins lymphoma. The method includes first reacting serum to be screened with one or more proteins present in a retrovirus characterized by (a) a round, nucleoid, C-type retroviral particle of approximately 100 nm in diameter, (b) an approximately 27,000 molecular weight p24 core protein, and (c) proteins of approximately 31,000 and 55,000 molecular weight. The presence of the virus is assayed by determining serum immunoreactivity with the distinctive protein(s).

In a preferred embodiment, the serum is reacted with fractionated proteins from the retrovirus. The presence of the virus is then determined by assaying for serum antibody binding to at least two proteins selected from the group of retrovirus proteins identified as p19, p27, gp31 and gp55.

These and other objects and features of the present invention will be more fully understood when the following detailed description of the invention is read in conjunction with the accompanying drawings.

BRIEF DESCRIPTION OF THE DRAWINGS

FIG. 7 (Parts A–C) shows 2-dimensional non-equilibrium SDS-PAGE analysis of radioiodinated 2F7 (A), 10C9 (B), and BLV (C);

DETAILED DESCRIPTION OF THE INVENTION

I. Isolation of 2F7 Retrovirus

Figure 1:
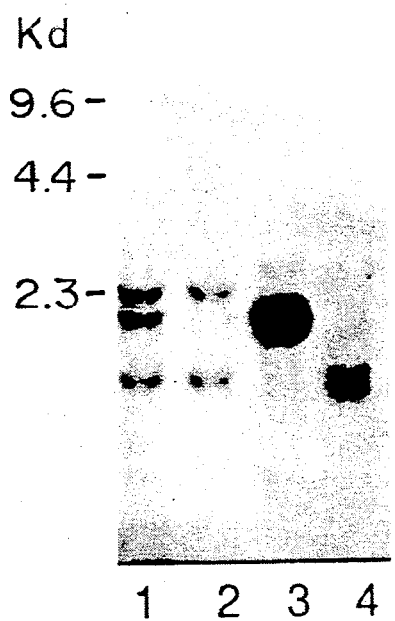
FIG. 1 shows a Southern blot analysis of DNA from 2F7 and AL-1 primary lymphoma tumor.

The cell line AL-I was established from a suspension of lymph node lymphocytes from a patient with AIDS associated Burkitt's lymphoma. Briefly, a human lymph node biopsy was minced and suspended through a 100 micron stainless steel screen in lymphoma culture medium (RPMI-1640, 10% human serum, 10M 2ME, 50 ug/ml Gentamicin). Cells were seeded at $2 \times 10$/ml in Primaria (Falcon) culture flasks and placed at 37° C., 5%$CO_2$. one-half of the media was replaced weekly. After approximately two months the cells had proliferated to the point of requiring passage into two flasks. Over the subsequent year fetal calf serum was gradually substituted for human serum and at the end of a year the cells required passage every three to four days at 1.5 dilutions.

Clone 12B7 was derived from a fusion between splenic lymphocytes from a Balb/C mouse immunized with purified HTLV-I virions and the nonsecretor mouse myeloma cell line 8653. The monoclonal IgG reacted with a 46 kd protein present on the surface of HTLV-I infected cells (C91/PL, HUT-102) but not present on normal lymphocytes or HTLV-I negative lymphomas (CEM, U8, JM).

Cytofluorographic analysis of this cell line showed the presence of cell surface IgM lambda on all cells and that rare cells stained with a monoclonal antibody (12B7) known to react specifically with HTLV-I infected cells. The original AL-1 cell line was therefore subcloned by limiting dilution and 12B7 reactive clones were identified.

Southern blot analysis of one 12B7-reactive cloned cell line, designated 2F7 (Example 1), demonstrated a bi-allelic immunoglobulin gene rearrangement pattern identical to that seen in the patient's original lymphoma tissue (FIG. 1), indicating the clonal nature of the 2F7 cell line and confirming that 2F7 was representative of the patient's original tumor.

To determine whether retroviruses were being produced by the 2F7 cell line, culture supernatants were concentrated by ultrafiltration and then subjected to equilibrium ultracentrifugation in a 20–50% sucrose gradient (Example 2). The material banding at a buoyant density of 1.14–1.16 g/cc was pelleted for examination by transmission electron microscopy (TEM), shown in FIG. 2. This analysis revealed numerous, pleomorphic membrane-bounded structures, approximately 100 nm in diameter, including many with morphologic features characteristic of C-type retroviral particles (Gallo).

Although the TEM morphology of the 1.14-1.16 g/cc banding fraction from 2F7 supernatants was consistent with C-type retroviral particles, reverse transcriptase activity in pelleted supernatants and banded material, as measured on 4 occasions, was only slightly above background (control 6,500±2,000, 2F7 samples, 15,000±4,000 counts per minute). While reverse transcriptase activity was reproducibly detected utilizing a standard assay employing magnesium as the required divalent cation (Hoffman), the low level of the activity precluded an accurate determination of the cation preference (Mg vs. Mn) as well as optimum cation concentration. Relatively low levels of reverse transcriptase activity in this range have been reported in the past for human leukemia viruses, perhaps reflecting either low level virion production and/or a high percentage of defective virions (Popovic).

Figure 3:
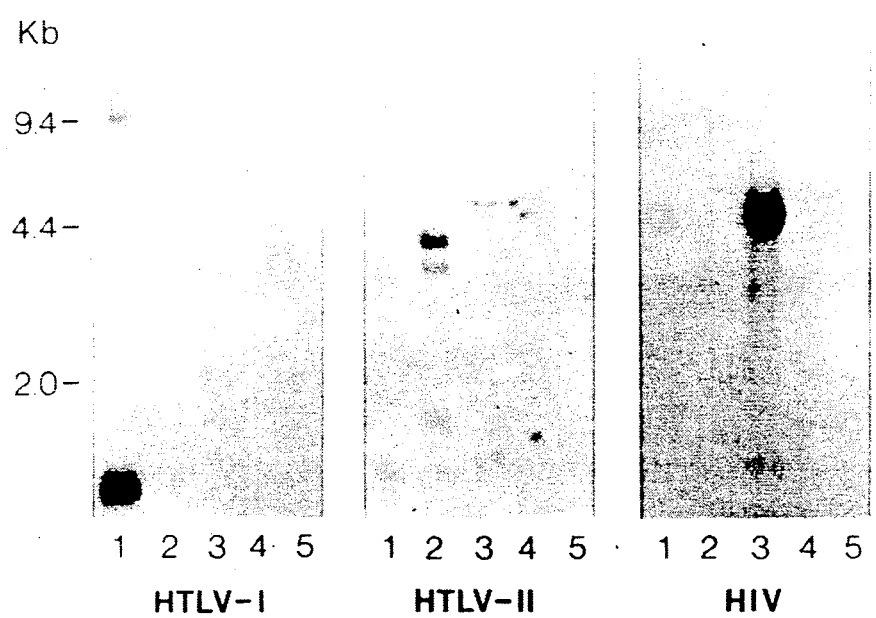
FIG. 3 shows Southern blots of HTLV-I, HTLV-II, and HIV DNA.

To test whether 2F7 contained DNA sequences homologous to known human retroviral genomes, 2F7 cellular DNA was hybridized with HTLV-I, HTLV-II and HIV-1 derived gene probes (Example 3). Southern blot hybridization using envelope gene probes from HTLV-I (Lane 1), HTLV-II (Lane 2), and HIV-1 (Lane 3) are shown in FIG. 3; Lane 4 in each section of FIG. 3 contains 2F7 cellular DNA. Although each retroviral gene probe hybridized with cellular DNA from an appropriate control cell line infected with that virus, no cross-hybridization with 2F7 cellular DNA was detected. Of note, the conditions of hybridization and washing clearly discriminated between the related but distinct HTLV-I and HTLV-II viruses.

The differential cross hybridization seen with HTLV-I and HTLV-II, despite the extensive serologic cross reactivity between the two viruses, helps to resolve the apparent paradox posed by the observation that no hybridization of the HTLV-I envelope gene probe to 2F7 cellular DNA was detected despite the fact that an HTLV-I reactive monoclonal antibody was used to select the 2F7 cell line.

Figure 4:
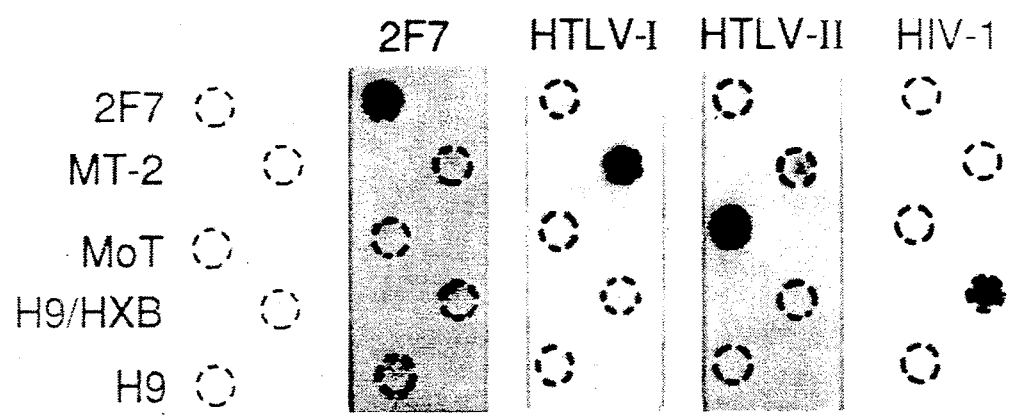
FIG. 4 shows RNA cytoblot analysis of virus-infected cell lines.

To test whether nucleic acid sequences from 2F7 virus preparations would cross hybridize with the RNA from cells infected with known human retroviruses, 2F7 viral cDNA was labelled and used as a probe (Example 4) in an RNA cytoblot analysis (Thomas)). As shown in FIG. 4, the 2F7 viral cDNA probe hybridized strongly with 2F7 RNA, but not substantially above background to any of the other RNAs tested, including HTLV-I, HTLV-II and HIV. FIG. 4 also demonstrates that HTLV-I, HTLV-II, and HIV gene probes hybridized appropriately with their homologous infected cell RNAs but not substantially with any other RNA, including 2F7. Of interest, the 2F7 viral cDNA probe did not hybridize above background to RNA derived from the patient's original tumor tissue. This finding is consistent with observations in other human leukemia virus associated tumors, in which tumor tissue from in vivo sources has not been found to express viral RNA (Suto).

Figure 5:
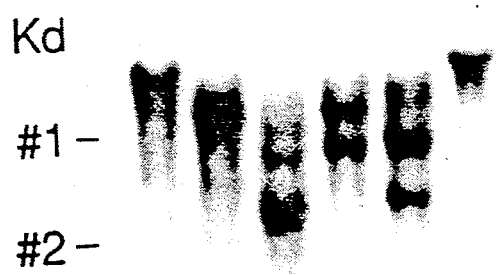
FIG. 5 shows Southern blot analysis of 2F7 cellular DNA with radiolabeled 2F7 cDNA.

Example 5 outlines Southern blot analysis of the cellular DNA of 2F7 which is illustrated in FIG. 5. FIG. 5 shows a restriction endonuclease digest of 2F7 cellular DNA hybridized with the same 2F7 viral cDNA probe used in FIG. 4, demonstrating significant hybridization to discrete species of 2F7 cellular DNA. Distinct patterns of hybridization were observed when different endonucleases were used. Lane 4 shows a double digest of 2F7 cellular DNA with HindIII and EcoRl, in which hybridizing DNA species of 3 kb and 12 kb can be identified. A BamHl digest (Lane 2) showed only one hybridizing DNA species, approximately 17 kb in size.

These data suggest that nucleic acids present in cDNA produced from a 2F7 virus preparation specifically recognized sequences contained within a 15-17 kb stretch of 2F7 cellular DNA. In preparations of uncut 2F7 cellular DNA (Lane 1), the 2F7 viral cDNA probe hybridized to a broad band that barely entered the gel. These data are consistent with the presence of an integrated form of 2F7 derived DNA, apparently smaller than 15 kb in length, within the 2F7 cell line. The 2F7 cDNA probe did not hybridize significantly to identical digests of cellular DNA from the human EBV infected cell line LB-2, suggesting that the sequences recognized within the 2F7 cellular DNA preparations are exogenous in nature, unrelated to the host cell genome, or to EBV.

II. Characterization of 2F7 and 10C9 Proteins

A second B-cell clone, 10C9, was independently isolated in an identical manner as 2F7 from a second patient. The fact that these viruses were isolated from lymphoma cells suggested that their biological properties were most consistent with that subfamily of retroviruses associated with tumorigenesis (oncoviruses). The characteristic type C morphology of the 2F7 and 10C9 retrovirus particles supports this categorization. The major virion proteins of 2F7 and 10C9 were analysed in comparison with the virion proteins of other known oncoviruses, including HTLV-I and Bovine leukosis virus (BLV).

BLV was used for most of the comparisons because of access to large quantities of highly purified virus, in contrast to the variable and often small quantities of HTLV-I produced by cultured cells (Palker). Also, in contrast to the T-cell malignancies caused by the other members of the oncovirus subfamily (ie, HTLV-I, HTLV-II, HTLV-V, STLV-I) (Yoshida), it is well established that BLV infection in cattle ultimately results in the development of B-cell lymphomas (Burny, 1986, 1987), and there appears to be a controversial association between human B-cell lymphomas in persons exposed to BLV (Ferrer).

Retrovirus particles from 2F7 and 10C9 culture supernatants were purified by equilibrium sucrose density gradient centrifugation, and the polypeptides analyzed by one-dimensional SDS-PAGE (Laemmli; Example 6, FIG. 6). A complex array of polypeptides were present in the 2F7 virus preparation, with major bands appearing at 65-80 kd, 50 kd, 45 kd, and 35 kd. Minor bands were also present at 27 kd and 30 kd. The 10C9 purified virus gave a similarly complex profile (data not shown). When these same virus preparations were radioactively labelled with $^{121}I$ (Fraker) and analyzed by two-dimensional non-equilibrium SDS-PAGE (O'Farrell; Example 7, FIG. 7), the most remarkable finding was the presence of 27 kd proteins in the 2F7 and 10C9 virus preparations which migrated to an identical isoelectric point as that of the BLV major virion core protein, p24. 2F7 also had a group of more basic proteins of approximately 12 kd, which comigrated with a similar group of proteins present in BLV.

The animal and human retroviruses all contain virion core structures composed of one predominant viral protein in size ranges between 24 kilodaltons (ie, BLV, HIV-1, HTLV-I), to 27 kilodaltons (Rous sarcoma virus) and 30 kilodaltons (murine leukemia viruses). Of all the virion core proteins, the structure of the major virion core protein is the most highly conserved (Ng). If 2F7 and 10C9 were retroviruses, they would also be expected to have a major virion core protein; in fact, the 2F7 and 10C9 27 kd species observed in the SDS-PAGE analyses shown in FIG. 7 which comigrated with the known major virion core protein of BLV (p24) were obvious candidates. To test whether 27 kd proteins (p27s) from 2F7 and 10C9 were homologous to the BLV p24, the purified proteins from the virions were compared by two different peptide mapping techniques.

Figure 8:
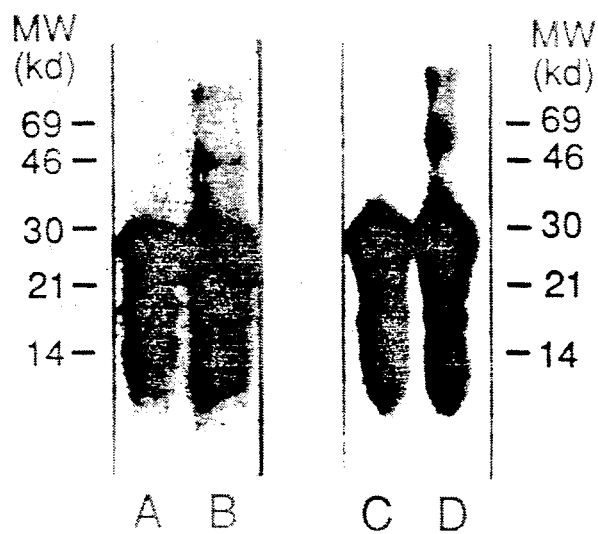
FIG. 8 shows staphylococcus V8 protease digestion of BLV p24 and 2F7 and 10C9 p27 proteins.
Figure 9A:
FIG. 9 (Parts A–D) shows the tryptic digest analysis of BLV p24 and 2F7 and 10C9 p27 proteins.
Figure 9B:
Figure 9C:
Figure 9D:
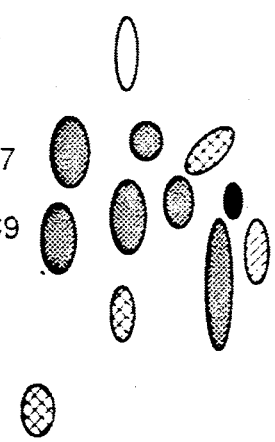

When subjected to limited Staphylococcal V8 protease digestion (Houmard; Example 8), the resultant peptides generated from the 2F7 and 10C9 p27s had almost identical patterns as those generated from BLV p24 (FIG. 8). Peptides unique to 2F7, 10C9 and BLV were also detected. A more exhaustive tryptic peptide fingerprinting technique (Kopchick; Example 9) was then employed to further analyze protein structure (FIG. 9).

In confirmation of the results generated by the Staphylococcal V8 protease digestion, at least six $^{121}$I-labelled tryptic peptides were shared by BLV p24 and 2F7 and 10C9 p27s. There were an additional three tryptic peptides shared by 10C9 and 2F7 p27s but absent from BLV p24, as well as a single tryptic peptide shared only by BLV p24 and 10C9 p27, and a unique tryptic peptide present in each of 2F7 and 10C9 p27s. Thus, the retrovirus of the present invention, as exemplified by the virus from 2F7 and 10C9 have at least nine tryptic peptides in common.

Figure 10:
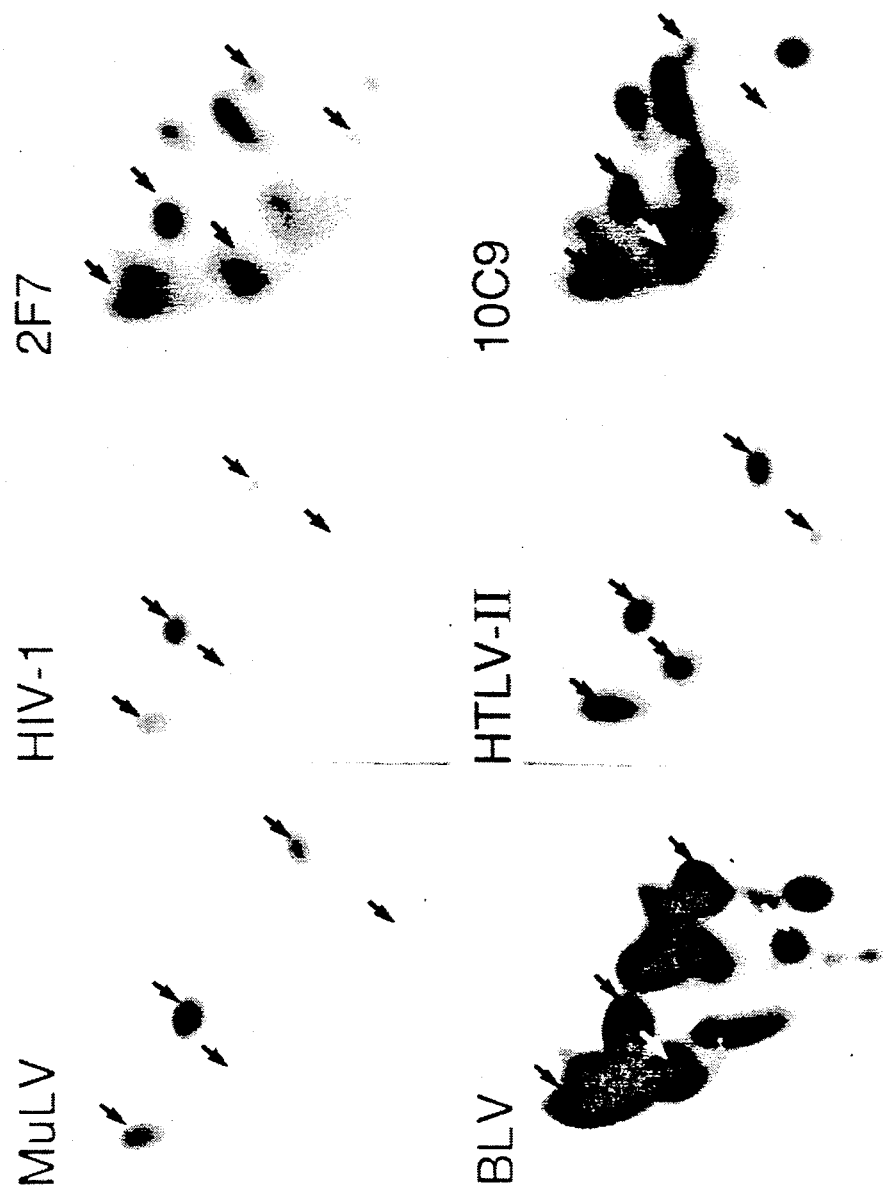
FIG. 10 shows a tryptic peptide analysis of retroviral p12 proteins.

The 12 kd proteins of 2F7 and 10C9 were also compared with those of HTLV-II, MuLV, BLV and HIV-1 (Example 10, FIG. 10). The tryptic peptide fingerprint of the p12s of the latter four viruses were nearly identical; in contrast, the p12s of 2F7 and 10C9 exhibited a much more complex tryptic fingerprint, in which a subset of peptides could be shown to comigrate with those of the p12s of the other retroviruses.

This more complex peptide profile would be consistent with an interpretation of the presence of at least two 12 kd proteins present in the 2F7 and 10C9 virus preparations, one of which shares homology with the other retroviral p12s.

Figure 11A:
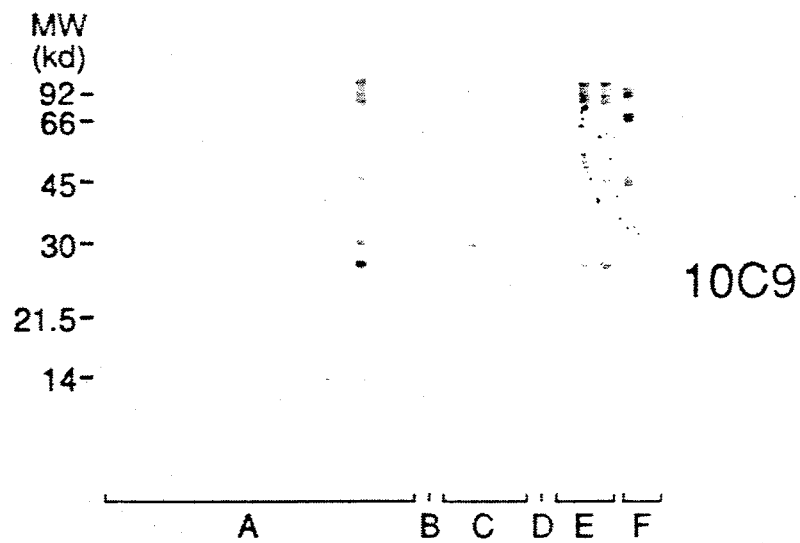
FIG. 11 (Parts A and B) shows human seroreactivity with 10C9 and 2F7 proteins.
Figure 11B:
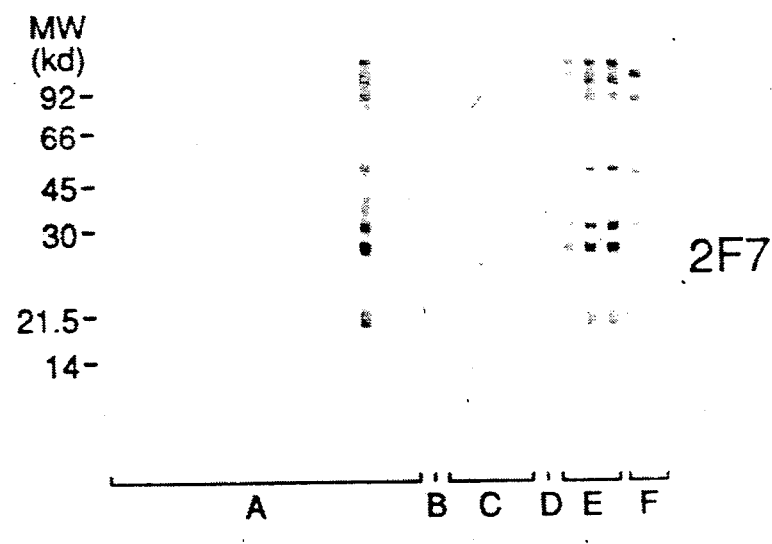

The serological characteristics of the 2F7 and 10C9 virion associated proteins was also investigated, as outlined in Example 11. FIG. 11 shows Western blots of normal human sera (NHS), serum from a woman with pelvic inflammatory disease (PID), serum from a Japenese patient with Adult T-cell leukemia/lymphoma (ATLL), serum from an intravenous drug user (IVDU), serum from a pregnant woman, and serum from an HIV-positive individual with non-Hodgkins lymphoma (H-NHL). As seen, the retroviruses obtained from both 2F7 and 10C9 are closely related to each other, as judged by their immunoreactivity with a variety of serotypes.

The 10C9 cell line was used as the antigen source for immunoblot analysis to avoid potential confusion by seroreactivity against EBV, since 2F7 is produced by an Epstein-Barr virus (EBV) infected cell line, whereas EBV is not present in 10C9 cells (data not shown).

Initial studies using sera from HIV-1 infected individuals with B-cell lymphoma suggested that atypical HTLV-I seroreactivity might be attributable to infection with these retroviruses. To test this possibility, all sera which had atypical HTLV-I seroreactivity were tested against 10C9 viral antigens. Only a few individuals who had strong reactivity against the 10C9 viral proteins were identified.

Figure 12:
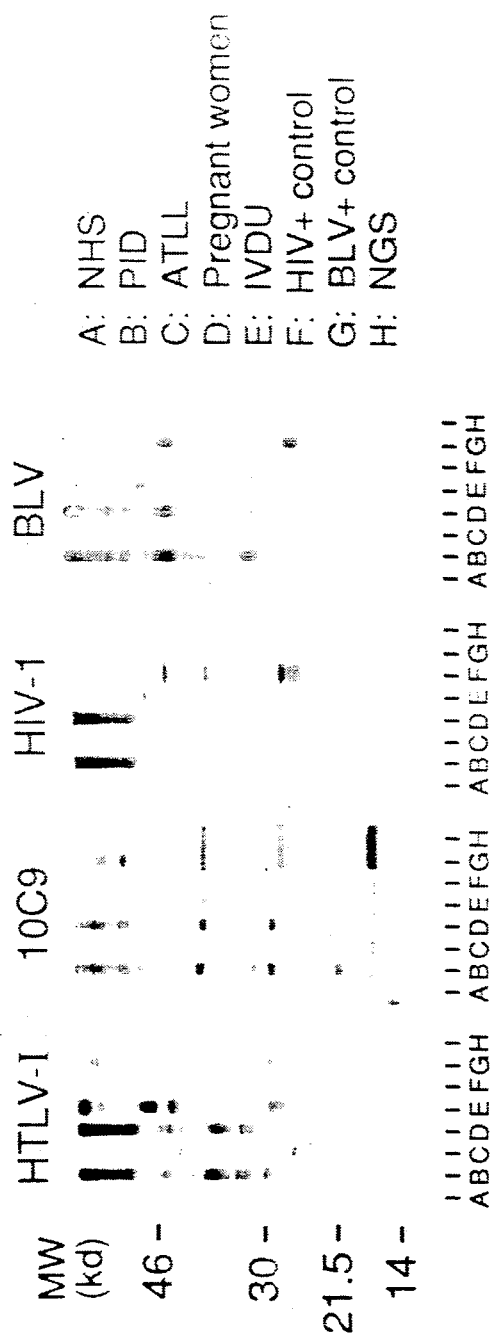
FIG. 12 shows seroreactivity with proteins from several retroviruses.

The seroreactivity pattern obtained by reacting sera from a variety of infected and non-infected sources against 10C9 and viral antigens of other known retroviruses (HTLV-I, HIV-1 and BLV) is shown in FIG. 12. HIV+ control is serum from an HIV-positive indivual, BLV+ control, serum from a BLV+ cow, and NGS, normal goat serum.

A typical seroreactivity was observed with HTLV-I viral antigens, no reactivity was observed with HIV-1antigens, and selected seroreactivity was observed with BLV antigens, notably with the envelope gp55 and gp31 proteins.

In summary, two closely related retroviruses, which are referred to herein as Human Lymphoma-Associated Virus (HuLAV) have been isolated and characterized. The HuLAV viruses isolated from AIDS-associated lymphoma tissue have putative major core proteins of 27 kd which have a high degree of structural homology with other known retroviruses. The seroreactivity of 10C9 seropositive individuals with BLV envelope proteins suggests that the putative envelope protein may share immunogenic epitopes with BLV.

Nontheless, a variety of evidence indicates that the HuLAV viruses of the present invention are distinct from BLV virus. First, SV8 and tryptic peptides unique to 2F7 and 10C9 p27 were observed. Secondly, 2F7 and 10C9 could not have been products of cross-contamination of tissue cultures by BLV since we do not cultivate BLV infected cells in vitro in our laboratory. Thirdly, the molecular characterization of the 2F7and 10C9 genomes (above) suggest significant sequence divergence from that of BLV, HTLV-I, HTLV-II. All of the above arguments support the inclusion of the 2F7/10C9 viruses in a distinct new family of retroviruses.

The following examples illustrate, but in no way are intended to limit the present invention.

EXAMPLE 1

Southern blot analysis of DNA from 2F7 and AL-1 primary tumor (HG)

This example describes a comparison of the genomic DNAs of subcloned cell line 2F7 and the original AL-1 tumor cell line.

DNA preparation

For extraction of DNA 2 to 5×107 lymphoma cells were lysed in 0.5 ml of lysis buffer (TE: 10 mM Tris, 1 mM EDTA, pH 6.5; 1% SDS). The lysate was treated with RNase (100 ug/ml) at 37' C. for one hour, with shaking. Proteinase K was then added to a final concentration of 100 ug/ml and incubated at 50° C. overnight after phenol extraction (25 phenol:24 Chloroform:1 isoamyl alcohol). The DNA-containing aqueous phase was collected. Sodium acetate was added to give a final concentration of 0.2M salt prior to adding ice cold ethanol. Ethanol precipitated-DNA was than centrifuged, and resuspended in TE. This method was used for all DNA preparations.

Southern blot hybridization

Southern blot analyses with an immunoglobulin gene $J_H$ probe (Korsmeyer) were performed on DNA isolated from the original HG tumor and the 2F7 cell line using previously described methods (Southern). DNA from the EBV transformed B lymphoblastoid cell line LB-2 and the T cell line CEM-CCRF served as positive and negative controls for $J_H$ rearrangement studies.

DNA samples (10 ug) were digested with 20 units of EcoR1 and 20 units of HindIII in appropriate buffers followed by chromatography and blotting to nitrocellulose (Schleicher and Schuell, Keene, N.H.). Hybridization probes were prepared from the $J_H$ gene probe insert by nick translation. 0.25 ug of each probe was labelled with $^{32}P$ dCTP (10 mCi/mM) by conventional methods.

DNA hybridization

All blots were pre-hybridized with 50% deionized formamide, 5% Denhardt's solution, 5% SCC, 0.1% SDS, and 100 ug/ml of denatured salmon sperm DNA, at 43° C. for at least four hours. $^{32}P$ labelled probes were incubated at 100° C. for ten minutes, immediately placed on ice for ten minutes, and then added to the pre-hybridization mix to give a final concentration of $2 \times 10^6$ cpm/ml. Blotted nitrocellulose was incubated in Seal-a-meal bags with labelled probe, at 43° C. overnight. After the overnight incubation, blots were washed twice in 2% SSC, 1% Denhardt's, shaking at 43° C. for thirty minutes prior to wash. The final two filter washes were with 0.1% SSC, 0.1% SDS, performed at 50° C. for thirty minutes each, with agitation. The filters were blotted dry, and exposed to X-ray film at −70° C. for 3 days. Lane 1: H6 original tumor DNA; Lane 2: 2F7 DNA; Lane 3 CEM-CCRF, T cell germ line control; lane 4: LB-2 B cell clone.

Comparison of lanes 1 and 2 demonstrates the clonal nature of the 2F7 cell line relative to the original tumor cell line.

EXAMPLE 2

Transmission electron microscopy of 2F7 viral particles 100 ml of supernatant from confluent 2F7 cells was spun at 15,000 g × 10 minutes to remove cellular debris, and was subsequently pelleted at 100,000 × g for 90 minutes. The pellet was resuspended in 100 ul of PBS layered over a continuous 20 to 50% sucrose gradient made in TN buffer (0.02M Tris pH 7.4, 0.1M NaCl). This gradient was spun for 16 hours at 100,000 × g; the gradient was tapped, and the density of fractions assessed by a refractometer. The fraction corresponding to 1.14–11.16 g/ml identified and pelleted for 90 minutes at 100,000 × g. Three percent EM grade glutaraldehyde in cacodylate buffer (100 ul) was added at 4° C. overnight, the pellet dislodged and post fixed in osmium tetroxide, then embedded in Epon 81. Ultra thin sections were stained with uranyl acetate-lead citrate.

Figure 2:
FIG. 2 is a transmission electron micrograph of 2F7 viral particles.

As can be seen in FIG. 2, round, nucleoid, C-type retroviral particles of approximately 100 nm are clearly present.

EXAMPLE 3

Analysis of 2F7 DNA for Homology with other Human Retroviruses

This example describes the comparison of 2F7 DNA to DNAs derived from HTLV-I, HTLV-II, and HIV.

DNA was prepared as in Example 1 from the following cell lines, and run (10 ug per lane) on 1% agarose gels. After transfer to nitrocellulose membranes Southern blot hybridization was performed (Southern). Lanes are: 1) MT-2 (HTLV-I); 2) MOT (HTLV-II); 3)H9/HXB (HIV); 4) 2F7; 5) CCRF CEM (no virus). $^{32}P$ labelled hybridization probes were: 1) HTLV-I; 2) the Sal-1/Xho-1 HTLV-I envelope gene segment; 3) HTLV-II full length envelope gene segment; 4) HIV-1 full length HXB-2 genome.

Each retroviral gene probe hybridized with cellular DNA from appropriate control cell lines infected with that virus, but no cross-hybridization with the cellular DNA derived from 2F7 was detected (Lane 4).

EXAMPLE 4

RNA cytoblot analysis of virus infected cell lines

This example describes the use of RNA cytoblot analysis to examine whether nucleic acid sequences from 2F7 virus preparations would cross-hybridize with the RNA from cells infected with known human retroviruses.

RNA analysis was performed by harvesting and disrupting $5 \times 10^6$ cells from each of the following cell lines: HG indicates the primary tumor which gave rise to the 2F7 cell line); 2F7; MT-2 (HTLV-I); MOT (HTLV-II); H9/HXB (HIV), and H9 (uninfected). Cells were lysed in 1.5 ml polypropylene microtubes using 0.4 ml of 50 mM sodium acetate buffer pH 4.8, 1% SDS. The solubilized cells were then extracted with an equal volume of 60° C. phenol equilibrated in 50 mM sodium acetate buffer pH 4.8. The aqueous phase of each sample was removed to a siliconized 1.5 ml microtube containing 50 ul of 3M sodium acetate buffer pH 5.2 and RNA precipitated by addition of two volumes of 100% ethanol. After pelleting, the RNA was denatured by incubating at 60° C., 15 minutes, in a solution of 6×SCC and 7.4% formaldehyde. The sample was then cooled and dotted onto 0.45 um nitrocellulose using a Bio-Rad dot blot apparatus. Prehybridization, hybridization and washing conditions were as described by Thomas. All hybridizations were performed using $2 \times 10^6$ cpm of the indicated probes (labelled with P32 nick translation of cDNA and probes). The same RNA dot blot was sequentially used for all hybridizations by removing hybrids through washing 2-4 times in 0.1×SCC, 0.1% SDS, 95°-100° C. Hybridization probes are indicated along the top of the figure. For HTLV-I, HTLV-II and HIV-1, appropriate subgenomic fragments encompassing the envelope gene were isolated off gels for use in labelling.

As shown in FIG. 4, the 2F7 viral DNA cDNA probes hybridized only with 2F7 RNA, but not significantly with any of the other tested RNAs.

EXAMPLE 5

I. Southern blot analysis of 2F7 cellular DNA with 32P-2F7 cDNA

This example describes the restriction nuclease digestion of 2F7 cellular DNA hybridized with the 2F7 viral cDNA probe of Example 4.

Southern blot analysis was carried out on different restriction endonuclease digests of 2F7 DNA as previously described. In lanes 1 and 6 above, 10 ug of uncut 2F7 DNA was run, in lane 2 BamHl digested 2F7 DNA, inlane 3 EcoR1 and HindIII digested 2F7 DNA, in lane 4 HindIII digested 2F7 DNA, in lane 5 PVU-2 DNA. The 32P-labelled 2F7 cDNA gene probe was the same as used in FIG. 4.

Distinct patterns of hybridization were observed with the different endonucleases and a broad band of hybridization was seen when the 2F7 cellular DNA was uncut; both of these results are consistent with the presence of an integrated form of 2F7 viral DNA.

EXAMPLE 6

One-dimensional SDS-PAGE analysis of purified HTLV-I and 2F7 virus

This examples describes a comparison of proteins purified from the 2F7 virus with HTLV-I associated proteins.

HTLV-I virus was purified from C91/PL (Miyoshi) culture supernatants which has been clarified of cellular debris by centrifugation (10,000×g, 15 minutes 4° C.), concentrated 100 fold by Amicon ultrafiltration, and chromatographed on a Sepharose 4B column (McGrath). The virus-containing column fractions were then layered onto a 15-60% continuous sucrose density gradient, centrifuged for 16 hours at 100,000×g, 4° C., the virus banding at a density of 1.14-1.16 g/dl collected, diluted with PBS, and pelleted by ultricentrifugation (100,000×g, 4° C., 90 minutes). The virus pellet was resuspended in SDS-PAGE sample buffer (Laemmli) and analyzed on a 9% SDS-PAGE. 2F7 virus (2F7V) was purified from culture supernatants in the same manner as HTLV-I, except that the Sepharose 4B chromatography step was omitted, and the 100-fold concentrated culture supernatants were instead pelleted through a 25% sucrose cushion/PBS (100,000×g, 4° C., 90 minutes). The resultant pellets were resuspended in PBS, homogenized, and overlaid on a 15-60% sucrose density gradient, with subsequent virus purification steps occurring as described for HTLV-I. Protein bands were visualized by Coomassie brilliant blue staining. The results are presented in FIG. 6: Lane 1—HTLV-I viral proteins; Lane 2 and 3—2F7 viral proteins. Molecular weights, in kilodaltons (kd), are as designated on the ordinate.

A complex array of polypeptides were present in the 2F7 virus preparation, with major bands at 65-80 kd, 50 kd, 45 kd, and 35 kd, and minor bands at 27 kd and 30 kd.

EXAMPLE 7

Two-dimensional non-equilibrium SDS-PAGE analysis

This examples describes a comparison of proteins purified from the 2F7 and 10C9 viruses with HTLV-I associated proteins using two-dimensional non-equilibrium SDS-PAGE.

FIG. 7 shows the results of two-dimensional non-equilibrium SDS-PAGE analysis of radioiodinated 2F7 (panel A), 10C9 (panel B) and BLV (panel C) viral proteins. 2F7 and 10C9 virions were purified as described in the legend to FIG. 1. BLV virions were purified by Sepharose 4B chromatography of a 100-fold Amicon ultrafiltration concentrated culture supernatant (Miyoshi). An aliquot of the most turbid virus containing fraction was radioiodinated (Fraker). Radioactive viral proteins were visualized by autoradiography using Kodak XAR 5 film. Molecular weights, expressed in kilodaltons (kd), are as indicated on the ordinate. The pH of the non-equilibrium electrofocusing gel is as indicated on the abscissa.

Most interesting is the presence of 27 kd proteins in the 2F7 and 10C9 virus preparations which migrate to an identical isoelectric point as that of the major virion core protein of BLV (p24).

EXAMPLE 8

Staphylococcal V8 protease digestion of BLV p24 and 2F7 and 10C9 p27s

This example describes the comparison of radioiodinated BLV p24 and 2F7 and 10C9 p27s. The proteins were isolated from one-dimensional SDS-PAGE of purified virions and subjected to limited SV8 protease digestion (Houmard).

In FIG. 8—Lane A: 2F7 p24 SV8 digest; Lane B: BLV p24 SV8 digest; Lane C: BLV p24 SV8 digest; Lane D: 10C9 SV8 digest. Molecular weights, expressed in kilodaltons (kd), are as indicated on the abscissa.

The peptides resulting from the limited Staphylococcal V8 protease digestion of 2F7 and 10C9 p27s have almost identical patterns as those generated from BLV p24.

EXAMPLE 9

Tryptic peptide analysis of BLV p24 and 2F7 and 10C9 p27s

This example describes the comparison of radioiodinated BLV p24 and 2F7 and 10C9 p27s, purified by one-dimensional SDS-PAGE of purified virions, and subjected to exhaustive tryptic digestion.

The radioactive proteins were cut from the gels and subjected to exhaustive trypsin digestion as previously described (Kopchick). Two-dimensional thin-layer separation of tryptic peptides was performed as previously described (Kopchick). The results of the tryptic digest are shown in FIG. 9. Panel A: BLV p24 tryptic peptide fingerprint; Panel B: 2F7 p27 tryptic peptide fingerprint; Panel C: 10C9 tryptic peptide fingerprint; Panel D: composite drawing defining shared and unique tryptic peptides.

These data support the previous conclusion obtained by the Staphylococcal V8 protease digestion of the relatedness of the BLV p24 and 2F7 and 10C9 p27s proteins; at least six tryptic peptides are shared by BLV p24 and 2F7 and 10C9 p27s proteins.

EXAMPLE 10

Tryptic peptide analysis of retroviral p12s

Radiodinated p12s of the various viruses, as indicated in the figure, were cut from the SDS-PAGE shown in FIG. 1, using the autoradiogram as the template. Trypsin digestion and two-dimensional fingerprinting was performed according to standard procedure. The results are shown in FIG. 10. The arrows in the 2F7 and 10C9 panel indicate those peptides which comigrate with similarly charged peptides present in the other retroviruses.

EXAMPLE 11

Human seroreactivity with retroviral proteins

Figure 6:
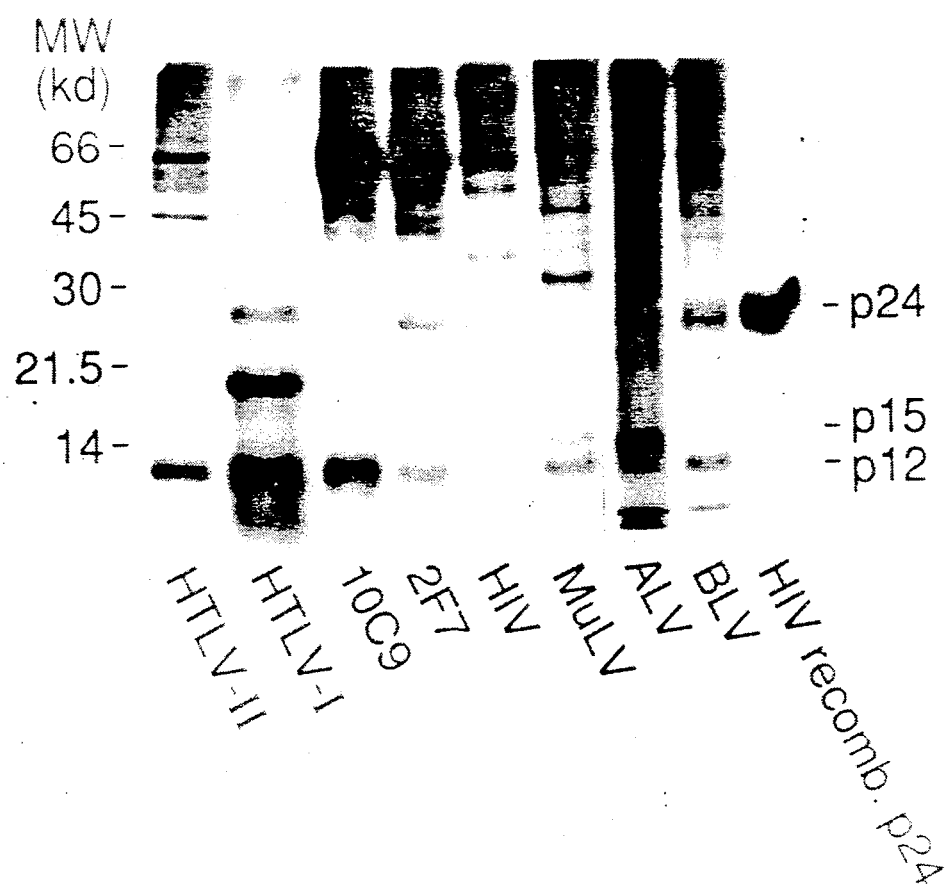
FIG. 6 shows one-dimensional SDS-PAGE analysis of several retroviruses.

HTLV-I (purified from C91/PL culture supernatants), HIV-1 (DV strain), BLV and 10C9 viruses were purified as described in the legend to FIG. 6, electrophoresed on 12% SDS-PAGE, and transblotted to nitrocellulose. Immunoblot analysis was performed as previously described. Sera tested included A) normal human serum, B) serum from a woman with pelvic inflammatory disease (PID), C) serum froma Japanese patient with Adult T-cell leukemia/lymphoma (ATLL), D) serum from an intravenous drug user (IVDU), F) serum from an HIV-I infected individual, G) serum from a goat immunized with BLV, and H) normal goat serum. All human sera were tested at a dilution of 1:50; the goat sera were tested at a dilution 1:1000. The results are shown in FIG. 12.

Although the invention has been described with respect to particular embodiments and methods, it will be clear that various modifications, methods, and uses are within the scope of the invention.

Lymphoma cell line 10C9 has been deposited as ATCC Deposit No. CRL 10236 and lymphoma cell line 2F7 has been deposited as ATCC Deposit No. CRL 10237 at The American Type Culture Collection, 12031 Parklawn Drive, Rockville, Md. 20852.

It is claimed:

1. A human retrovirus isolated from cultured non-Hodgkins human B-lymphoma cells, characterized by:
   a) C-type retroviral particle of approximately 100 nm diameter;
   b) an approximately 27,000 molecular weight p24 core protein;
   c) proteins of approximately 31,000 and 55,000 molecular weight; and
   d) where said retrovirus further has the characteristics of a retrovirus isolated from a lymphoma cell line selected from the group consisting of ATCC CRL 10236 and ATCC CRL 10237.

2. The retrovirus of claim 1, which is further characterized by a p24 core protein tryptic digest map which contains the eleven tryptic digest fragments shown in FIG. 9C.

3. The retrovirus of claim 2, which has the characteristics of the retrovirus isolated from the cell line designated ATCC CRL 10236.

4. The retrovirus of claim 1, which is further characterized by a p24 core protein tryptic digest map which contains the ten tryptic digest fragments shown in FIG. 9B.

5. The retrovirus of claim 4, which has the characteristics of the retrovirus isolated from the cell line designated ATCC CRL 10237.

6. A lymphoma cell line isolated from a suspension of lymph node lymphocytes from a patient with AIDS associated, non-Hodgkins lymphoma and containing a retrovirus characterized by:
   a) a C-type retroviral particle of approximately 100 nm diameter;
   b) an approximately 27,000 molecular weight p24 core protein;
   c) proteins of approximately 31,000 and 55,000 molecular weight; and
   where said lymphoma cell line is selected from the group consisting of ATCC CRL 10236 and ATCC CRL 10237.

7. The cell line of claim 6, designated ATCC CRL 10236, in which the retrovirus is characterized by a p24 core protein whose tryptic digest map contains the eleven tryptic digest fragments shown in FIG. 9C.

8. The cell line of claim 6, designated ATCC CRL 10237, in which the retrovirus is characterized by a p24 core protein whose tryptic digest map contains the ten tryptic digest fragments shown in FIG. 9B.

* * * * *